United States Patent
Burnett et al.

(10) Patent No.: US 12,109,036 B2
(45) Date of Patent: Oct. 8, 2024

(54) DEVICES AND METHODS TO MEASURE GASTRIC RESIDUAL VOLUME

(71) Applicant: Gravitas Medical, Inc., San Francisco, CA (US)

(72) Inventors: Daniel R. Burnett, San Francisco, CA (US); Marcie Hamilton, San Francisco, CA (US); Evan S. Luxon, Omaha, NE (US); Alexander Vergara, San Francisco, CA (US); Saheel Sutaria, El Cerrito, CA (US)

(73) Assignee: Gravitas Medical, Inc., Berkeley, CA (US)

( * ) Notice: Subject to any disclaimer, the term of this patent is extended or adjusted under 35 U.S.C. 154(b) by 89 days.

(21) Appl. No.: 17/675,903

(22) Filed: Feb. 18, 2022

(65) Prior Publication Data

US 2022/0167910 A1 Jun. 2, 2022

Related U.S. Application Data

(63) Continuation of application No. 15/222,670, filed on Jul. 28, 2016, now Pat. No. 11,284,832, which is a
(Continued)

(51) Int. Cl.
*A61B 5/00* (2006.01)
*A23L 33/00* (2016.01)
(Continued)

(52) U.S. Cl.
CPC ............ *A61B 5/4238* (2013.01); *A23L 33/30* (2016.08); *A23L 35/00* (2016.08); *A61B 1/2736* (2013.01);
(Continued)

(58) Field of Classification Search
CPC . A61B 5/4238; A61B 5/6847; A61B 5/14546; A61B 5/486; A61B 5/742;
(Continued)

(56) References Cited

U.S. PATENT DOCUMENTS

| | | |
|---|---|---|
| 4,836,214 A | 6/1989 | Sramek |
| 4,921,481 A | 5/1990 | Danis et al. |

(Continued)

FOREIGN PATENT DOCUMENTS

| | | |
|---|---|---|
| WO | WO 1992/017150 | 10/1992 |
| WO | WO 2012/174102 | 12/2012 |
| WO | WO 2015/120285 | 8/2015 |

*Primary Examiner* — Rex R Holmes
(74) *Attorney, Agent, or Firm* — Levine Bagade Han LLP

(57) ABSTRACT

Devices and methods to measure gastric residual volume (GRV) are described where at least one additive component (a GRV indicator) may be dispersed in a body lumen such as a stomach. The GRV indicator may changes a physical (chemical, electrical, thermal, mechanical, optical, etc.) characteristic within the stomach by a measureable degree. This degree of change and/or the rate of return to the previous state, may be used to determine the GRV of a patient. The determined GRV can also be used to automatically or semi-automatically control the patient's feeding rate and/or volume and/or frequency to adequately nourish the patient but avoid complications. The physical characteristic(s) may also be used to detect that the feeding catheter or tube is in the correct location (ie stomach vs lung or esophagus.

44 Claims, 16 Drawing Sheets

Related U.S. Application Data continuation of application No. PCT/US2015/014839, filed on Feb. 6, 2015.

(60) Provisional application No. 61/936,804, filed on Feb. 6, 2014.

(51) Int. Cl.
| | |
|---|---|
| *A23L 35/00* | (2016.01) |
| *A61B 1/273* | (2006.01) |
| *A61B 5/01* | (2006.01) |
| *A61B 5/03* | (2006.01) |
| *A61B 5/107* | (2006.01) |
| *A61B 5/145* | (2006.01) |
| *A61J 15/00* | (2006.01) |

(52) U.S. Cl.
CPC ............. *A61B 5/01* (2013.01); *A61B 5/036* (2013.01); *A61B 5/1073* (2013.01); *A61B 5/14507* (2013.01); *A61B 5/14532* (2013.01); *A61B 5/14539* (2013.01); *A61B 5/14546* (2013.01); *A61B 5/4848* (2013.01); *A61B 5/486* (2013.01); *A61B 5/6847* (2013.01); *A61B 5/6852* (2013.01); *A61B 5/6865* (2013.01); *A61B 5/6871* (2013.01); *A61B 5/742* (2013.01); *A61J 15/008* (2015.05); *A61B 2562/0204* (2013.01)

(58) Field of Classification Search
CPC ... A61B 5/6852; A61B 5/6865; A61B 5/6871; A61B 1/2736; A61B 5/01; A61B 5/036; A61B 5/1073; A61B 5/14507; A61B 5/14532; A61B 5/14539; A61B 5/4848; A61B 2562/0204; A61J 15/008; A23L 35/00; A23L 33/30

See application file for complete search history.

(56) References Cited

U.S. PATENT DOCUMENTS

| | | | |
|---|---|---|---|
| 6,334,064 | B1 | 12/2001 | Fiddian-green |
| 6,357,447 | B1 | 3/2002 | Swanson et al. |
| 7,818,155 | B2 | 10/2010 | Stuebe et al. |
| 8,147,486 | B2 | 4/2012 | Honour et al. |
| 8,613,702 | B2 | 12/2013 | Feer et al. |
| 8,986,230 | B2 | 3/2015 | Nishtala |
| 9,179,971 | B2 | 11/2015 | Kirschenman |
| 9,226,878 | B2 | 1/2016 | Elia et al. |
| 9,295,395 | B2 | 3/2016 | Elia et al. |
| 9,532,739 | B2 | 1/2017 | Bennett-Guerrero |
| 9,610,227 | B2 | 4/2017 | Elia |
| 9,642,779 | B2 | 5/2017 | Elia et al. |
| 9,713,579 | B2 | 7/2017 | Elia et al. |
| 11,284,832 | B2 | 3/2022 | Burnett et al. |
| 2002/0103425 | A1 | 8/2002 | Mault |
| 2005/0096514 | A1 | 5/2005 | Starkebaum |
| 2007/0207554 | A1 | 9/2007 | Lin et al. |
| 2008/0097179 | A1 | 4/2008 | Russo |
| 2008/0167607 | A1 | 7/2008 | Pfeiffer et al. |
| 2010/0030133 | A1* | 2/2010 | Elia ............... A61B 5/4836 604/35 |
| 2010/0249663 | A1 | 9/2010 | Nishtala |
| 2010/0274225 | A1* | 10/2010 | Nishtala ............ A61B 5/4238 604/514 |
| 2012/0016256 | A1 | 1/2012 | Mabary et al. |
| 2012/0089128 | A1* | 4/2012 | Rotella ............ A61J 15/0015 604/529 |
| 2012/0277619 | A1 | 11/2012 | Starkebaum et al. |
| 2013/0225946 | A1 | 8/2013 | Feer et al. |
| 2016/0113843 | A1 | 4/2016 | Elia et al. |
| 2016/0129223 | A1 | 5/2016 | Kirschenman |
| 2017/0202750 | A1 | 7/2017 | Elia |
| 2018/0161249 | A1 | 6/2018 | Elia et al. |

\* cited by examiner

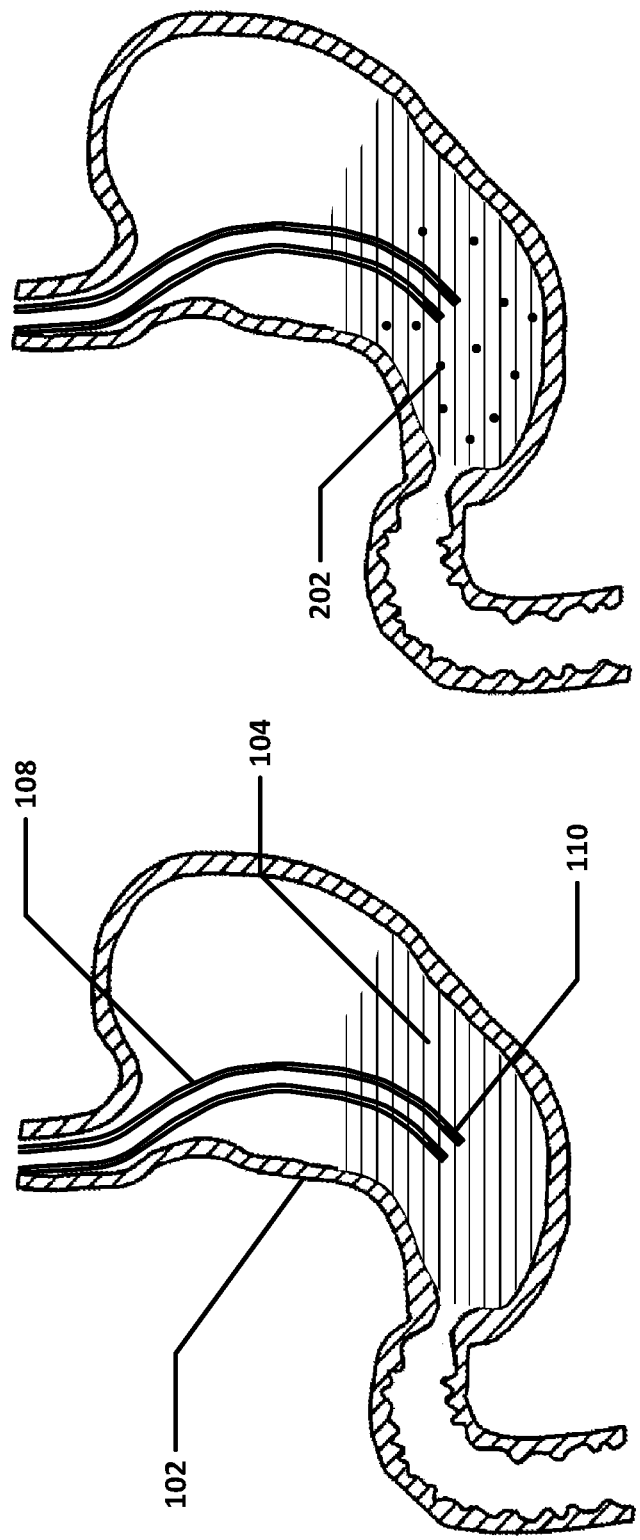

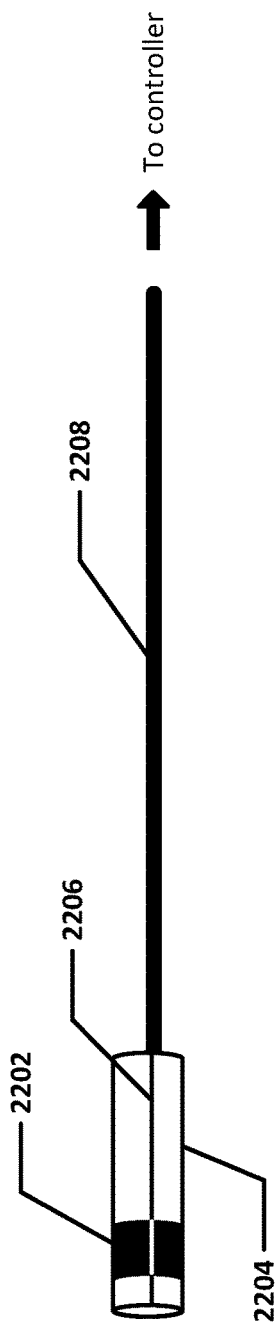
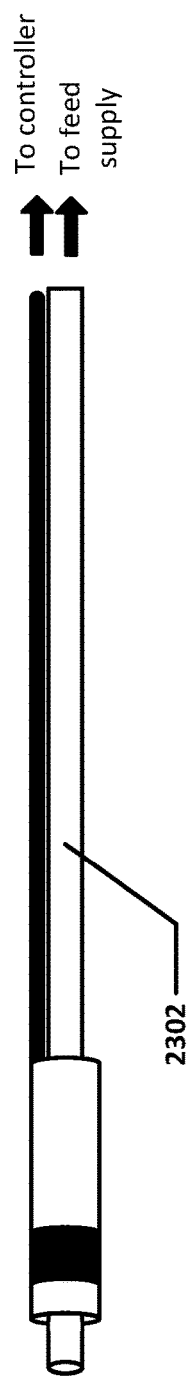
FIG. 22
FIG. 23
FIG. 24

DEVICES AND METHODS TO MEASURE GASTRIC RESIDUAL VOLUME

CROSS-REFERENCE TO RELATED APPLICATIONS

This application is a continuation of U.S. patent application Ser. No. 15/222,670 filed Jul. 28, 2016 (now U.S. Pat. No. 11,284,832), which is a continuation of International Application No. PCT/US2015/14839 filed Feb. 6, 2015, which claims the benefit of priority to U.S. Provisional Application No. 61/936,804 filed Feb. 6, 2014, each of which is incorporated herein by reference in its entirety.

FIELD OF THE INVENTION

The present invention relates to the measuring of gastric volume.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

Enteral feeding through a feeding tube allows patients to receive nutrition when he/she cannot receive nutrition through the mouth, cannot swallow safely or to provide supplemental nutrition. Current standard of care require periodic monitoring of the gastric residual volume (GRV) after feeding. GRV is the volume of residual gastric contents that remain in the stomach after a certain period of time has elapsed after feeding via a feeding tube. The concern is that high GRV values may indicate pulmonary aspiration, a critical issue that could lead to pneumonia with serious consequences. Usually these GRV measurements occur every 4-6 hours, and particularly during the first few days of enteral feeding to allow acceptance of the feeding tube.

The current standard method of determining GRV is via aspiration from a nasogastric tube. There are several issues with the current methods of determining GRV including:

1) Aspiration of contents to measure GRV is a burden on nursing staff. Even with expertise in the procedure, the process takes 5 minutes. With this repeated every 4-6 hours for every patient requiring GRV monitoring.

2) The process of aspirating gastric contents through manual mechanical means may increase the incidence of pulmonary aspiration.

3) Lack of standardization of means to manually measure GRV, whether through aspiration by syringe, low-wall suction, gravity drainage or other method, introduce errors in measurement.

A solution is needed which addresses these and other issues with measuring GRV in patients.

SUMMARY OF THE INVENTION

The present invention is a GRV measuring device and methods which determine the volume of gastric content by introduction of at least one additive component (a GRV indicator) that is dispersed and then changes a physical (chemical, electrical, thermal, mechanical, optical, etc.) characteristic within the stomach contents by a measureable degree. The degree of change of this physical characteristic, and/or the rate of return to the previous state, may be used to determine the GRV of a patient. If the GRV is small, the magnitude of change will likely be greater, and the rate of change of this physical characteristic back to baseline will be slower. If the GRV is large, the magnitude of change will likely be smaller, and the rate of return to baseline will be faster. The determined GRV can also be used to automatically or semi-automatically control the patient's feeding rate and/or volume and/or frequency to adequately nourish the patient but avoid complications. The physical characteristic(s) may also be used to detect that the feeding catheter or tube is in the correct location (ie stomach vs lung or esophagus).

One variation of an apparatus for determining a gastric residual volume may generally comprise an elongate body which may define at least one lumen therethrough, a medium having one or more GRV indicators which may be in fluid communication with the at least one lumen, one or more sensors positioned along the elongate body such as at or near a distal tip of the elongate tube, wherein the one or more sensors are configured to measure a change in a parameter of the GRV indicators, and a controller in communication with the one or more sensors, wherein the controller is configured to determine a GRV based on the change in the parameter of the GRV indicators.

In use generally, such an apparatus may be used to determine the GRV by positioning the elongate body which may define at least one lumen therethrough into the body lumen, introducing the medium having one or more GRV indicators such as through the at least one lumen and into the body lumen, and sensing the one or more GRV indicators via one or more sensors positioned along the elongate body such as at or near a distal tip of the elongate body. The one or more GRV indicators may be monitored for a change in a parameter of the GRV indicators and the GRV of the stomach may be determined based on the change in the parameter of the GRV indicators.

BRIEF DESCRIPTION OF THE DRAWINGS

FIG. 1 shows an embodiment of the GRV measuring device in a human stomach.

FIG. 2 shows a stomach into which a substance containing a concentration of a GRV indicator is introduced.

FIG. 10 shows sensor(s) of the GRV measuring device in the pylorus

FIGS. 20-24 show embodiments of the GRV measuring device.

DETAILED DESCRIPTION OF THE INVENTION

Figure 4:
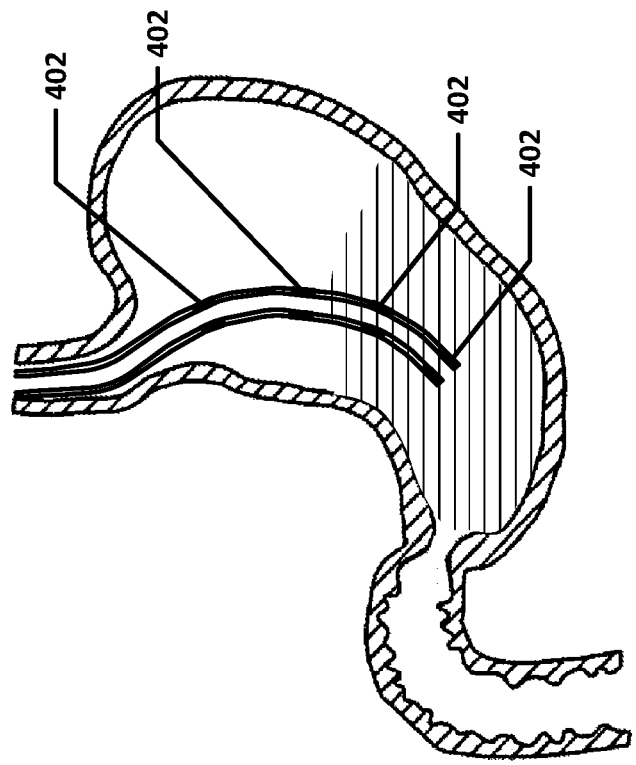
FIG. 4 shows an embodiment of the GRV measuring device where sensors are located along the length of the catheter or tube.

FIG. 1 shows an embodiment of the GRV measuring device in a human stomach. GRV measuring device 108 in this embodiment is a catheter, or tube containing at least one lumen. The GRV measuring device also includes sensor or sensors 110, in this embodiment, at or near the distal tip of the GRV measuring device. The lumen may be used for feeding the patient, and/or introducing a GRV indicator into stomach 102. Stomach contents 104 include gastric secretions, nutrients which were previously present in the stomach, nutrients that have been added to the stomach via the GRV measuring device or otherwise, as well as any GRV indicators used to determine the GRV of the stomach.

GRV indicators may include a substance at a higher or lower temperature than the stomach contents, a substance at a higher or lower pH than the stomach contents, a substance at a higher or lower O2 concentration than the stomach contents, a substance at a higher or lower CO2 concentration than the stomach contents, a substance at a higher or lower ion (such as Magnesium) concentration than the stomach contents, a substance at a higher or lower glucose concentration than the stomach contents, a substance at a higher or lower viscosity than the stomach contents, etc. Additional GRV and/or stomach entry indicators include electrical properties (conductance, resistance, current generation based on the acid level, impedance, etc.) that will increase or decrease depending on the ratio of stomach acid to tube feed in the stomach. Other GRV indicators are also possible and some are described in other embodiments herein.

GRV indicators may be introduced through the lumen of GRV measuring device 108 into stomach contents 104. Sensor or sensors 110 then can measure the change in properties of the stomach contents to determine the Gastric Residual Volume, or GRV, of the stomach.

For example, if a substance is introduced into the stomach which is at a higher or lower temperature than the stomach contents, the sensor(s) can measure the magnitude of change, and/or the rate of change of temperature of the stomach contents to determine the GRV. Both the rate of initial change, and the rate of change back to the pre-introduction state can be measured, as well as the magnitude of change. In general, the change from the maximum change, back to the pre-introduction level, is a slower change and easier to measure, but either change can be measured. After the GRV indicator is introduced, and the maximum level of the GRV indicator has been measured, the rate of change of the indicator, or slope of the temperature vs. time curve, can be measured. A relatively steep slope indicates a higher GRV, where a relatively shallow slope indicates a lower GRV. The same can be done with concentration and other GRV indicator types. For example, if the GRV indicator is glucose, the sensor(s) would measure the concentration of glucose within the stomach contents and the change in concentration over time.

Alternatively, a bolus of a substance at a fixed temperature (or concentration, etc., depending on the GRV indicator) can be introduced into the stomach and the temperature (or concentration, etc.) of the stomach contents can be measured as soon as the contents have had a chance to mix. The relatively immediate magnitude of change in temperature or concentration may also be an indicator of the GRV of the stomach. The lower the GRV, the greater the impact the introduction of the GRV indicator will have on the stomach contents. The higher the GRV, the lower the impact will be, resulting in a lower magnitude of measured change of the GRV indicator.

Another embodiment of the GRV measuring device includes a temperature changing mechanism as part of the device. In this embodiment, the temperature of the stomach contents may be altered by either a heating or cooling element. For example, GRV measuring device 108 may include a heating element (not shown) which heats the contents of the stomach. The change of temperature is measured over time and the rate and/or magnitude of the temperature change as the stomach contents heat and/or cool can be used to determine the GRV of the stomach.

Another variation of this embodiment of the GRV measuring device measured pH instead of temperature. A substance of a certain pH (higher or lower than that of the stomach contents) can be introduced into the stomach, and the change in pH measured over time to determine the GRV of the stomach.

A controller (not shown) may be used as part of the GRV measuring device to record and/or interpret the various levels of GRV indicator(s) measured by sensors within the stomach. The controller may also use the GRV info to control feeding volume/rate/frequency/contents.

FIG. 2 shows a stomach into which a substance containing a concentration of a GRV indicator is introduced and the concentration measured over time within the stomach contents. In this embodiment, the sensor(s) measure concentration instead of temperature. For example, GRV indicator 202 in this embodiment may be glucose, or magnesium, or any other suitable substance, the concentration of which can be measured.

Figure 14:
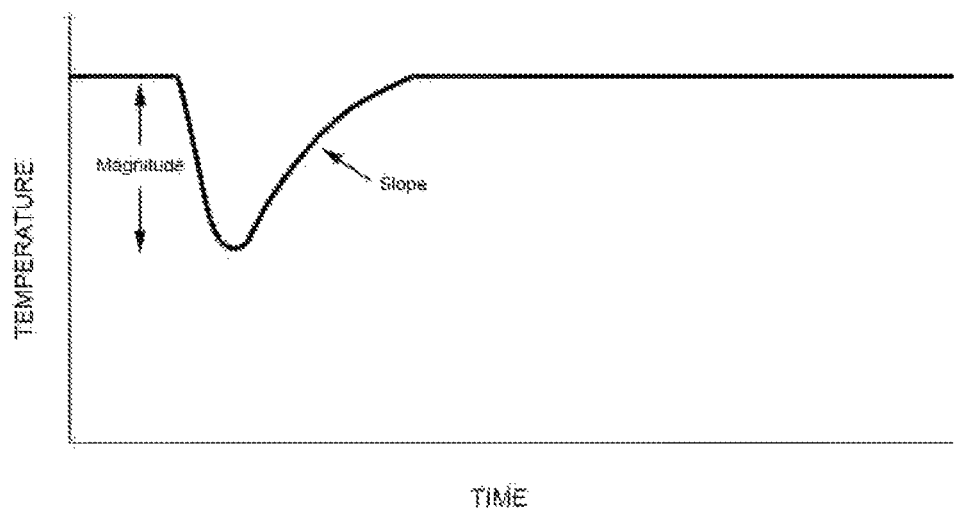
FIG. 14 shows a graph of the temperature of the stomach contents over time as sensed by sensor(s) after a bolus of cold substance is introduced into the stomach.

FIG. 14 shows a graph of the temperature of the stomach contents over time as sensed by the sensor(s) and recorded and/or interpreted by the controller after a bolus of cold liquid is introduced into the stomach. The magnitude of the temperature drop and the slope of the gradual temperature rise back to normal can be used either together, or separately, to determine the GRV of the stomach.

Figure 15:
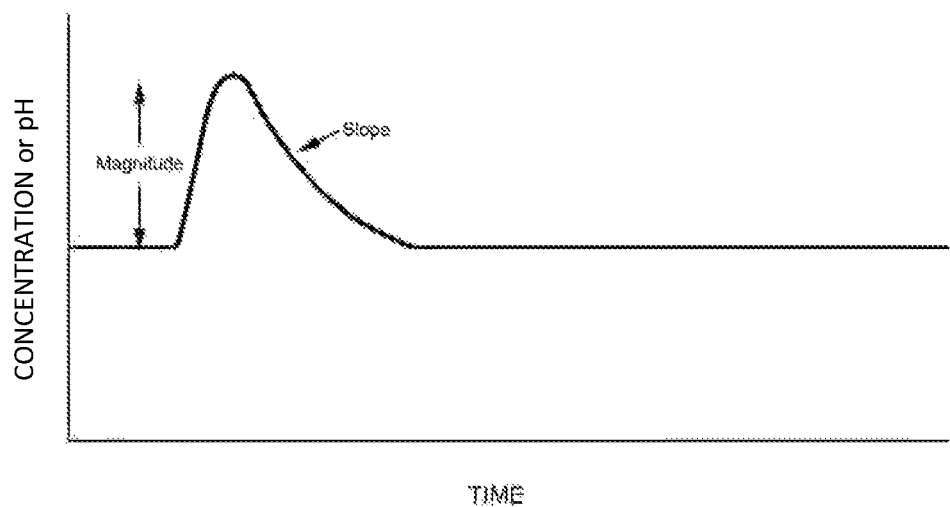
FIG. 15 shows a graph of the concentration or pH of a GRV indicator over time after introduction into the stomach.

FIG. 15 shows a similar graph for the introduction of a GRV indicator for which the concentration or pH is measured. After introduction of the GRV indicator into the stomach, the concentration or pH rises, and then gradually returns to normal over time. Again, the magnitude of the change and the slope of the return to normal of the concentration or pH of the GRV indicator within the stomach can be used together, or separately, to determine the GRV of the stomach.

Figure 16:
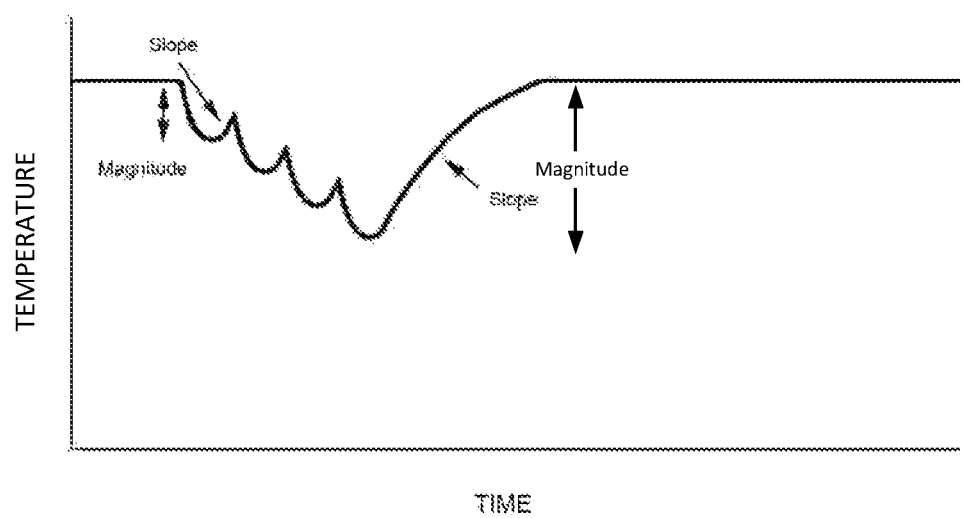
FIG. 16 shows a graph of the temperature of the stomach contents over time as sensed by sensor(s) after multiple boluses of cold substance are introduced into the stomach.

FIG. 16 shows a graph of the temperature of the stomach contents over time as sensed by the sensor(s) and recorded and/or interpreted by the controller after multiple boluses of cold liquid are introduced into the stomach. Note that in this example, the magnitude and/or slope of the graph after each bolus may be utilized by the controller, in addition to the overall magnitude and slope of the boluses combined. Multiple boluses may be used with other GRV indicators as well.

Figure 3:
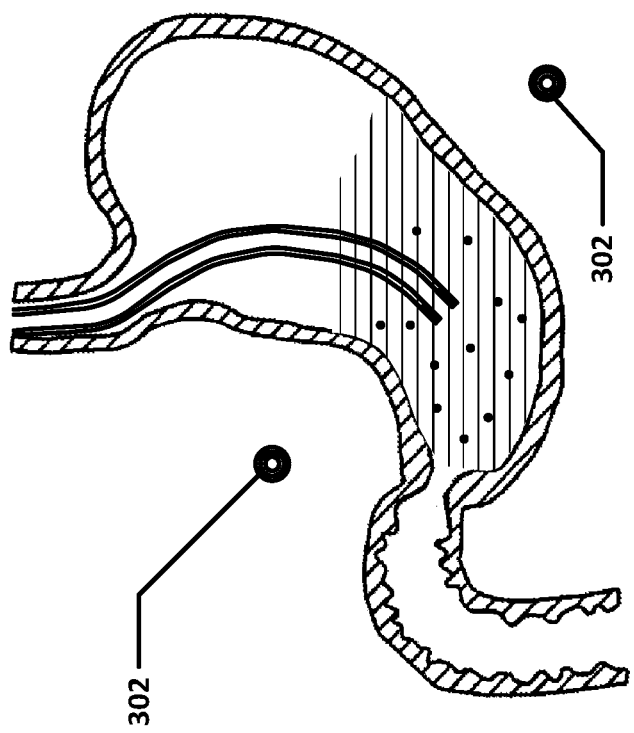
FIG. 3 shows an embodiment of the GRV measuring device where sensors are outside of the stomach.

FIG. 3 shows an embodiment of the GRV measuring device where sensors 302 are outside of the stomach, and preferably outside the patient's body. This embodiment is limited to GRV indicators which can travel through tissue such as temperature, radiation, sound waves, magnetic substances, etc.

FIG. 4 shows an embodiment of the GRV measuring device where the sensors are located along the length of the catheter or tube. In this embodiment, the GRV indicator can be measured at different locations within the stomach, providing more information regarding the GRV. For example, assuming the patient is upright and the stomach contents are at the bottom of the stomach, the GRV indicator readings at the more proximal end of the GRV measuring device would be much lower, or even null, where the measurements at the distal end of the device would change over time as the GRV indicator is introduced and diluted by the stomach contents. Depending on the different GRV indicator measurements at different locations along the GRV measuring device, more information can be obtained about the volume of the contents in the stomach. For example the device may be able to determine that the stomach is approximately half full etc.

Figure 6:
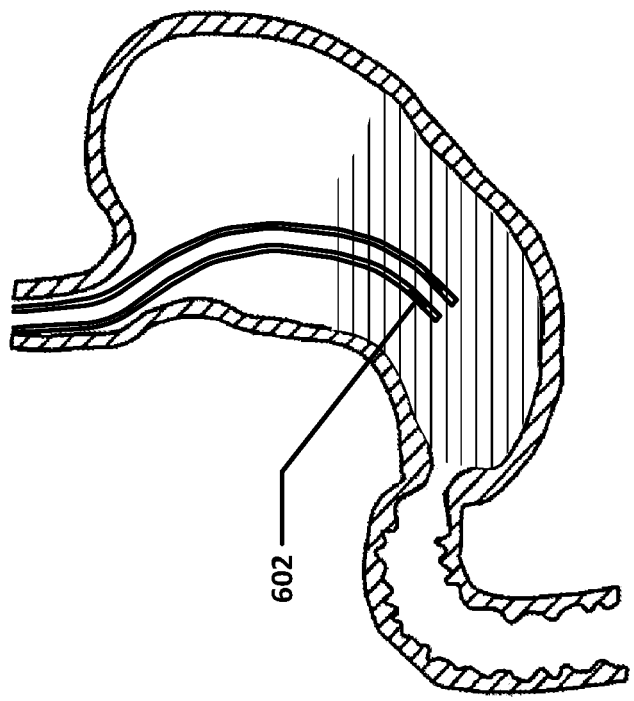
FIGS. 5 and 6 show embodiments of the GRV measuring device where sensor(s) are at different location.
Figure 5:
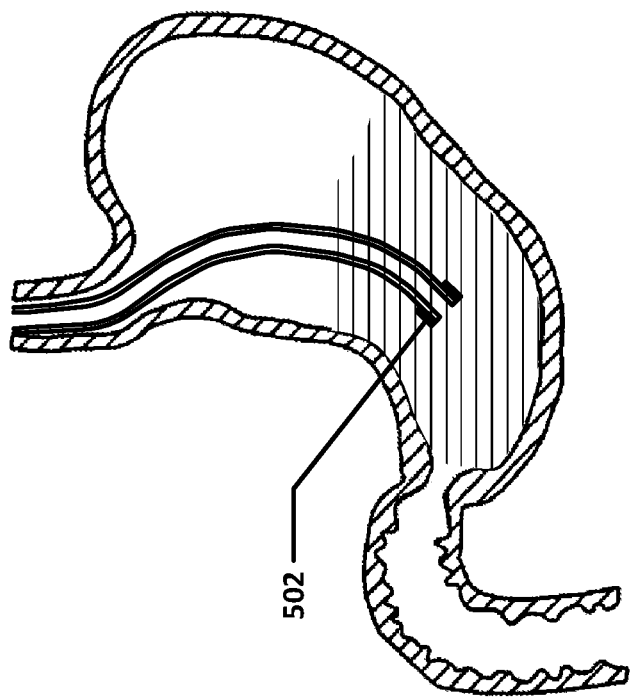

FIGS. 5 and 6 show embodiments of the GRV measuring device where the sensor(s) are at different location. FIG. 5 shows sensor(s) 502 on the outside of tube/catheter. Note that in any of the embodiments herein the sensor(s) may run radially around the tube/catheter or be on one or more sides of the catheter/tube. This, and other embodiments, also allows for a separate feeding tube to be inserted through the GRV measuring device (not shown). This may be desirable where a standard feeding tube is being used. Also, it is possible to insert the GRV measuring device into the patient over a feeding tube that is already in place. This would be advantageous when it is not known at the time of placement of the feeding tube that the GRV measuring device will be used.

FIG. 6 shows sensor(s) 602 embedded in the wall of the GRV measuring device. This embodiment offers the advantage of a smooth transition on both the outside and the inside of the GRV measuring device. Note that the sensor(s) in any of the embodiments may be at any location along the length of the GRV measuring device.

Figure 7:
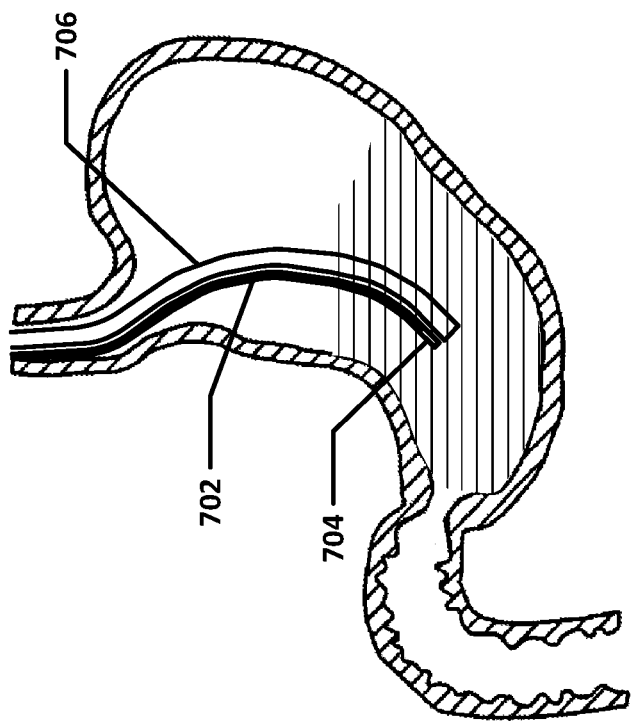
FIG. 7 shows an embodiment of the GRV measuring device which is separate from a feeding tube.

FIG. 7 shows an embodiment of the GRV measuring device which is separate from the feeding tube. In this embodiment, feeding tube 706 may be inserted into the patient separately from GRV measuring device 702. GRV measuring device in this embodiment may or may not have a lumen. Since the feeding of the patient occurs through a separate tube, the size of the GRV measuring device can be much smaller and be inserted alongside of the feeding tube. In fact, GRV measuring device in this embodiment may be similar dimensions to a guide wire (down to 0.5 mm or less, or 1.0 mm or less, or 2.0 mm or less) with sensor(s) 704 at its distal end or along its length. In this embodiment the GRV indicator may be introduced through the separate feeding tube.

Figure 8:
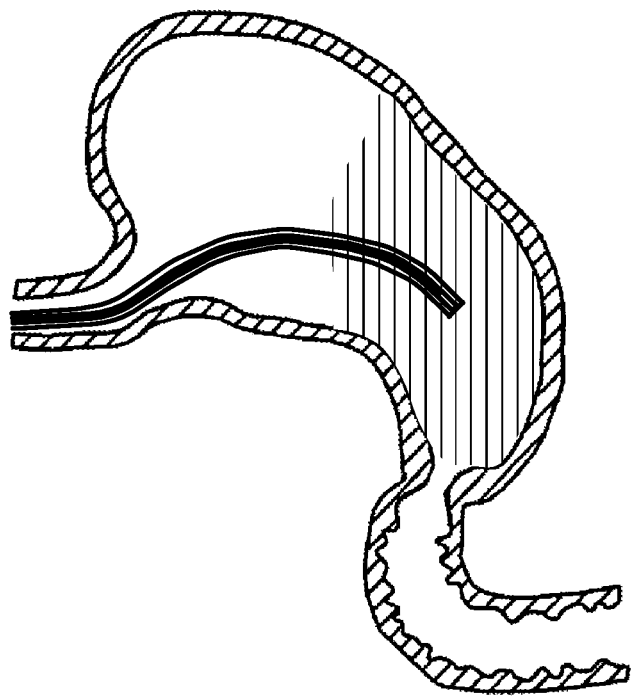
FIG. 8 shows a GRV measuring device where the GRV measuring device is inserted through a feeding tube.

FIG. 8 shows a GRV measuring device similar to that of FIG. 7, however in this figure, the GRV measuring device is inserted through the feeding tube. This configuration has the advantage of easily being inserted after the feeding tube is already in place. In this and any of the embodiments the GRV measuring device may be introduced only periodically before or after the GRV indicator is introduced into the stomach. In this way, the extra bulk of the GRV measuring device does not significantly interfere with the feeding process through the feeding tube. Alternatively, the GRV measuring device may be small enough to not adversely impact the flow of nutrients or other substances through the feeding tube. The GRV measuring device in this and other embodiments may have a curved tip, or a J-tip to help maneuver it through and out the opening of a feeding tube.

Note also that the GRV measuring device shown here may also be used to confirm location of the device in the stomach, vs. the lungs or esophagus (discussed in more detail herein). In this scenario, the GRV measuring device may be placed first, with confirmation of placement in the stomach by using sensor(s). The feeding tube may then be placed over the GRV measuring device so that the placement of the feeding tube in the stomach is also confirmed. In this embodiment, the GRV measuring device would need to be long enough (or extendable) to allow the user to thread the feeding tube over the GRV measuring device and into the stomach. For example, in an embodiment where the feeding tube is threaded over the GRV measuring device, the GRV measuring device (or extended GRV measuring device) would preferably be at least about twice the length of the feeding tube. For a child, the length may be at least about 75 cm, for an adult the length may be at least about 180 cm, or at least about 200 cm or at least about 280 cm. A GRV measuring device extension may be a wire that is either permanently, or removably, attachable to the end of the GRV measuring device to extend it.

In embodiments of the GRV measuring device where it is placed after the feeding tube, the length can be shorter, for example, for a child, at least about 40 cm, or for an adult, at least about 95 cm, or at least about 110 cm, or at least about 140 cm.

Figure 10:
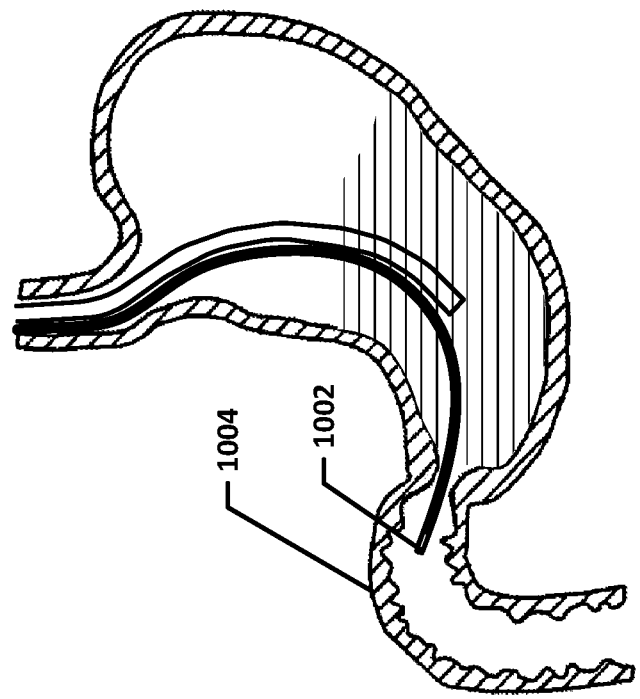
FIGS. 9 and 10 illustrate how the sensor(s) of the GRV measuring device may be located at various places relative to the feeding tube.
Figure 9:
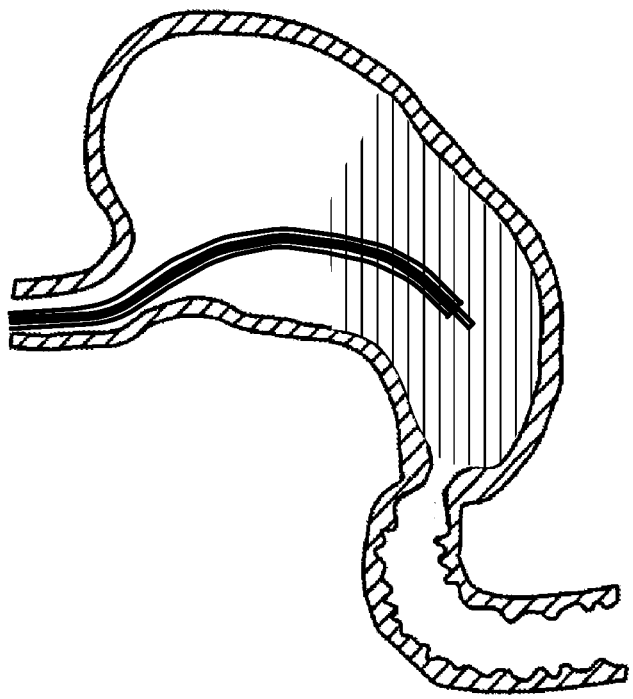

FIGS. 9 and 10 illustrate how the sensor(s) of the GRV measuring device may be placed at various places relative to the feeding tube. This may help obtain cleaner measurements after introduction of the GRV indicator. For example, if a heated substance is introduced through the feeding tube, it may be advantageous to have the sensors of the GRV measuring device some distance away from the exit of the feeding tube, both to protect the sensors from extreme heat, but also to get a cleaner temperature reading. More mixing of stomach contents will have occurred the further from the source of the GRV indicator introduction the sensor(s) are.

Alternatively the sensors may be placed within the feeding tube when the GRV indicator is introduced through the feeding tube to obtain a baseline reading of the temperature/concentration/pH etc. of the GRV indicator. The sensors may then be moved into the stomach contents to obtain the changing readings which will be used to determine GRV. Alternatively, the GRV measuring device may have sensors along its length to achieve the same thing. There may be other advantages to moving the GRV measuring device during the measurement process. Measuring the GRV indicator at different places within the stomach and/or stomach contents will provide more information about the stomach contents.

FIG. 10 shows sensor(s) 1102 of the GRV measuring device in the pylorus 1004. In this embodiment, the stomach content volume is estimated through direct measurement of the input volume (enteral feeding material) and output volume (pylorus transit). The amount of material entering and passing through the pylorus may be measured with a volumetric flow meter, or Doppler ultrasound, or optics, or any other suitable technology. In one embodiment, after magnetic materials are introduced into the stomach, the movement of the materials induces a current as it passes the pylorus transit which can be measured either within the pylorus, or outside of the patient.

Note that in any of the embodiments herein, the GRV measuring device may be outside of, inside of, incorporated into or completely separate from the feeding tube.

Figure 12:
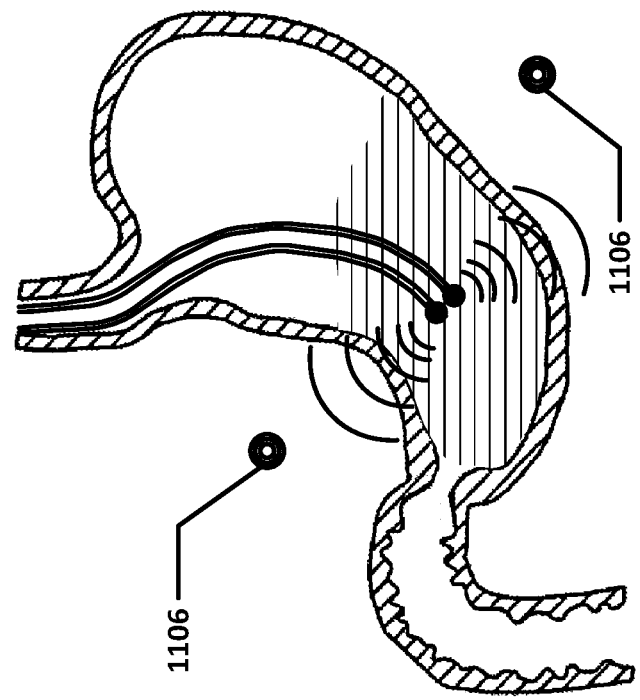
FIGS. 11-13 show embodiments of the invention in which there is at least one transmitter and/or receiver to track location of the device within the stomach and/or stomach contents.
Figure 11:
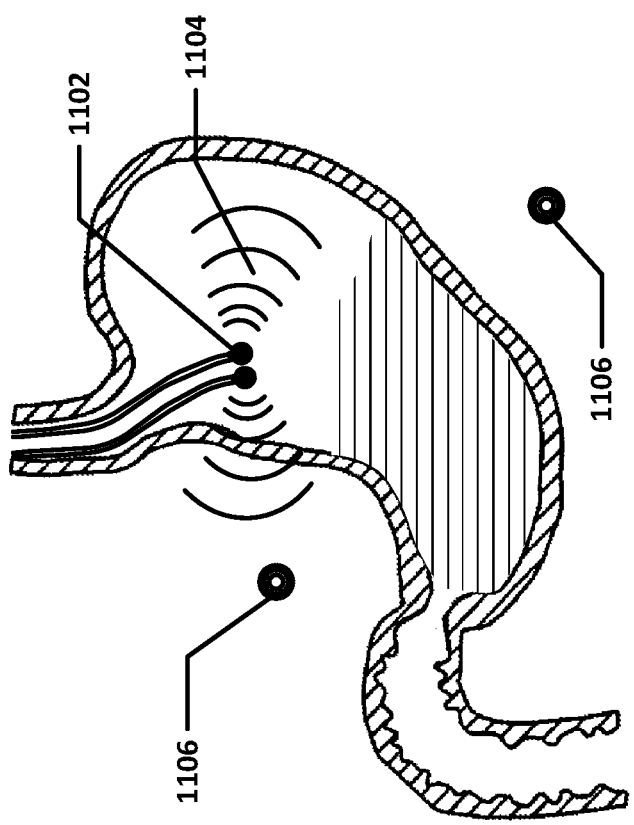
Figure 13:
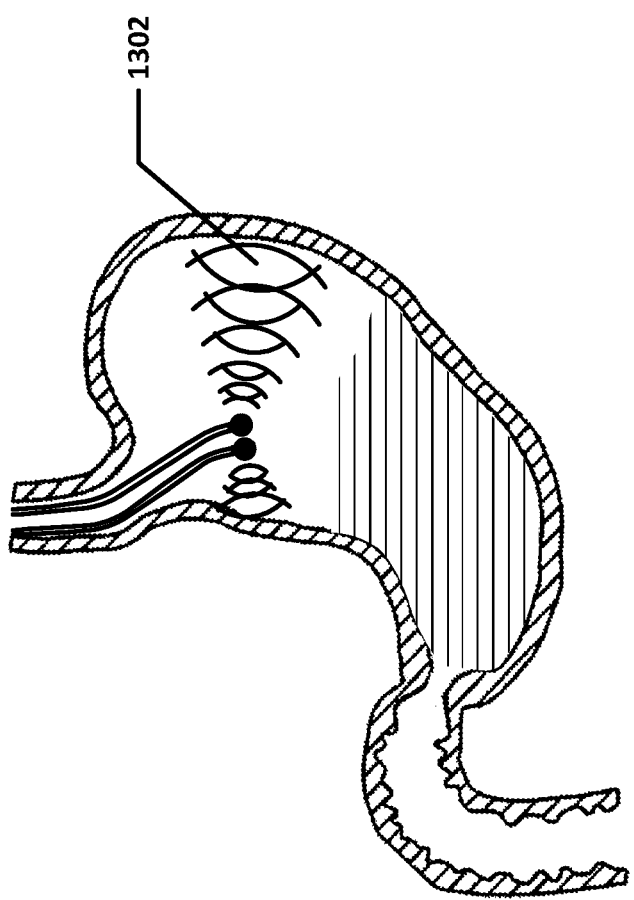

Other embodiments of the invention are shown in FIGS. 11-13. In these embodiments, the GRV measurement device is also used to locate the device, or a feeding tube, within the stomach to ensure proper feeding and GRV measurements. In these embodiments transmitters 1102 give off a signal which is detected by location receivers 1106. The transmitters may be separate from the sensor(s) shown in other embodiments, however both may be present on the GRV measuring device (note that the sensor(s) are not shown in FIGS. 11-13). The location receivers may exist outside the body as shown in FIGS. 11 and 12, or they may be part of the GRV measuring device, as shown in FIG. 13. The transmitted signal may be a sound signal, an ultrasound signal, a pressure signal, or any other suitable signal. Alternatively, or in addition, pH, temperature, or any of the GRV indicator signals may be used. The location receivers receive the signal either through the tissue, as shown in FIGS. 11 and 12, or after reflected signal 1302 has bounced off of the walls of the stomach and possibly the stomach contents, as shown in FIG. 13. The embodiment of the GRV measuring device in FIG. 13 includes both the transmitters and the location receivers on the device within the stomach.

FIGS. 11 and 12 show the transmitter in the empty part of the stomach and the stomach contents, respectively. The signal received when the transmitter is in these two different locations will be very different, and will aid in locating the tip of the feeding tube. The transmitters may be at the tip of the feeding tube, and/or may be elsewhere relative to the tip of the feeding tube.

Figure 17:
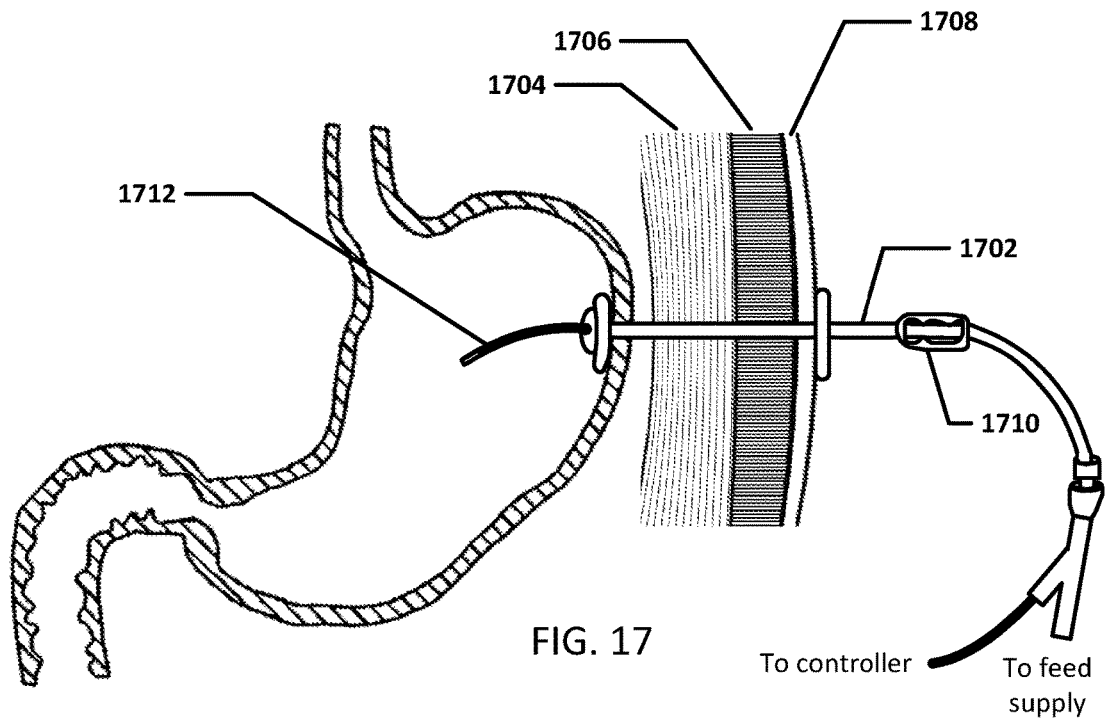
FIGS. 17 and 18 show embodiments of the GRV measuring device for use percutaneously.
Figure 18:
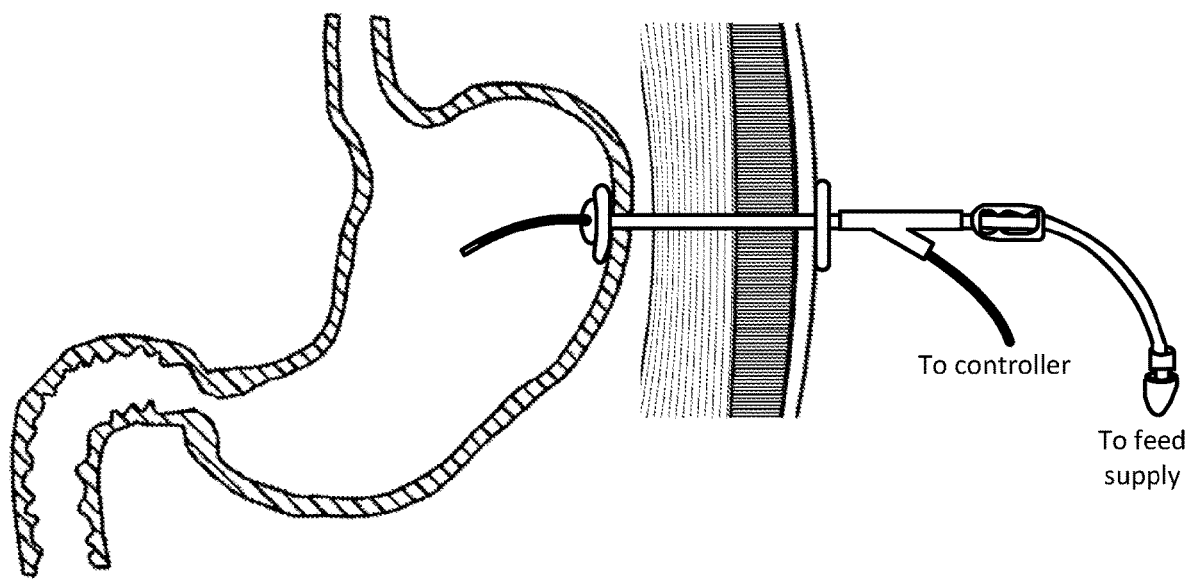

FIGS. 17 and 18 show embodiments of the GRV measuring device being used percutaneously. For example, the GRV measuring device can be used as, or in conjunction with, a Percutaneous Endoscopic Gastrostomy, or PEG, tube. In this situation the feeding tube goes through the abdomen of the patient, directly into the stomach, to feed the patient. Shown here is PEG tube 1702 going through skin 1708, fat 1706 and muscle 1704 and through the stomach wall so that the tip of the PEG tube is in the stomach. The GRV measuring device may be incorporated into the PEG tube, or may be separate as shown here. GRV measuring device 1712 is shown here being used through the inside of a PEG tube. In this and other embodiments the GRV measuring device is connected to a controller to record and/or interpret the measurements sensed by the sensors.

In this and other embodiments, GRV measuring device may be in the stomach throughout feeding, or it may be introduced periodically when measurements are desired. Restrictor 1710 may be used to control the flow of nutrients into the stomach. The restrictor may be controlled by the controller in a feedback loop so that nutrients are only introduced when the GRV is at or below a certain level. Nutrients may also be automatically limited when the GRV is at or above a certain level. These levels may be preset, or may be set by the controller and can be adjusted as necessary. This type of feedback control also allows for bolus feeding vs. continuous feeding which is more physiologically representative.

FIG. 18 is similar to FIG. 17 except that the entrance point for the GRV measuring device is between the patient and the resistor. This allows the resistor to be more easily used when the GRV measuring device is in place.

Note that the embodiments in FIGS. 17 and 18 can be used with a standard PEG tube. Alternatively, the GRV measuring device may be incorporated into a PEG tube.

Figure 19:
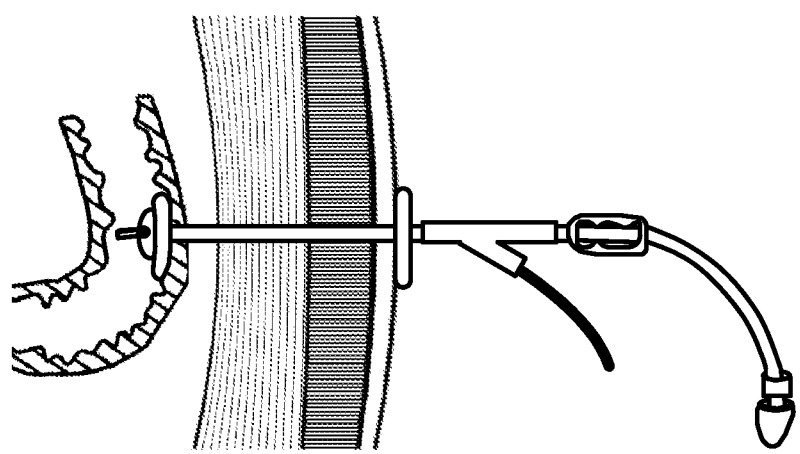
FIG. 19 shows an embodiment of the GRV measuring device for use with a jejunostomy tube.

FIG. 19 shows an embodiment of the GRV measuring device for use with a jejunostomy tube. In this embodiment the feeding tube enters the intestines rather than the stomach. Similar to other embodiments herein, the GRV measuring device may be used with a standard jejunostomy tube, or may be incorporated into a jejunostomy tube.

Figure 20:
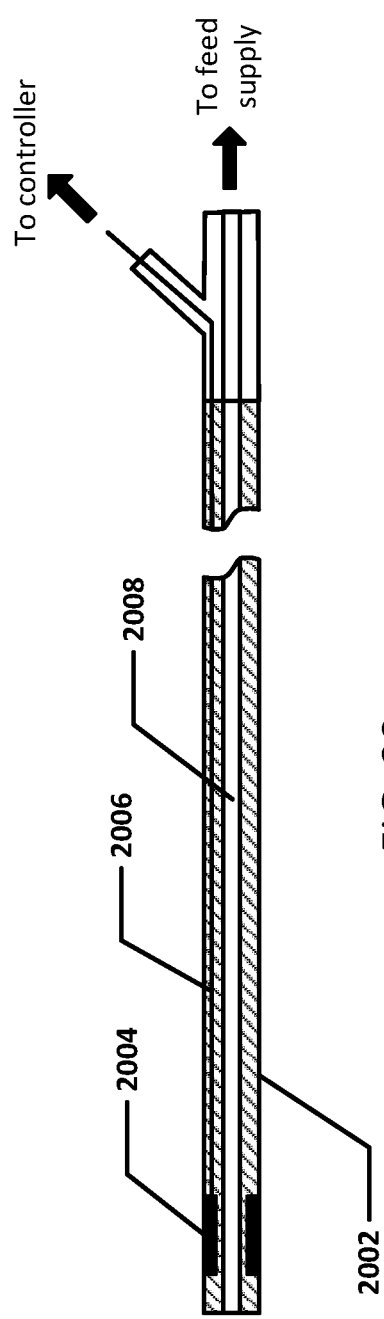

FIGS. 20-24 show detailed embodiments of the GRV measuring device. FIG. 20 shows an embodiment of the GRV measuring device which is incorporated into a feeding tube. Device shaft 2002 includes sensor or sensors 2204, measurement communication line 2006, which may be a metal wire, as well as feeding lumen 2008. Sensor(s) 2004 measure the temperature, pH, concentration etc. of the GRV indicator in the stomach after the indicator is introduced through the device or created by the device. For example, a fluid below body temperature may be introduced into the stomach through lumen 2008. The magnitude of the change of temperature within the stomach is measured by sensor(s) 2004, as well as the rate of return to normal temperature. This information is transferred along communication line 2006, along shaft 2002 back to the controller. The controller may control the feed supply either with user input, or automatically, depending on the gastric volume analysis of the controller.

Note that sensor(s) 2004 may be placed anywhere along the length of the device. Also note that sensor(s) may be placed on either the inside of the device (within lumen 2008) or on the outside, or both. Having separate sensors on both the inside and outside of the device may allow measurements of the untainted GRV indicator as it is entering the stomach (inside sensors) as well as measurements of the change in the GRV indicator over time (outside sensors). These sensors may be the same sensor, where it measures both inside the device, and outside the device. Also note that there may be a barrier or insulator between the sensor and either the inside of the device, or the outside of the device. This would allow the sensor to measure the GRV indicator on either the inside of the device or the outside of the device without being tainted.

Alternatively the GRV measuring device may cause a cooling of the stomach contents with a cooling element (not shown) on the device, and measure the resulting magnitude and rate of temperature change to determine gastric volume.

In another example, the pH of the stomach contents may be measured to determine gastric volume. A substance of a known pH (which may be the feeding substance itself) is introduced into the stomach, and the sensor(s) measure the change in pH and the rate of return to normal pH, send the information back to the controller, and the controller can then determine gastric volume.

In another embodiment, the GRV measuring device may use more than one GRV indicator. For example, both temperature and pH may be used. In this example, measurement of one GRV indicator may be used to confirm the measurement of the other GRV indicator for a more accurate result. In addition, the measurements may be taken at different locations to assure stomach content mixing and/or to improve accuracy. Other GRV indicators may be combined in a similar manner.

Figure 21:

FIG. 21 shows another embodiment of the GRV measuring device. This embodiment is designed to be used with a feeding tube, either alongside it or through the lumen of a feeding tube. This embodiment may be of a relatively small diameter (down to 0.5 mm or less, or 1.0 mm or less, or 2.0 mm or less) so that it does not substantially impede the flow of nutrients to the patient through the feeding tube, or is not difficult to insert into the patient alongside a feeding tube. Shaft 2102 is preferably relatively stiff, similar to a guidewire, and incorporates the signal communication from sensor(s) 2104. Shaft 2102 may be made out of metal such as stainless steel or other appropriate material. In this embodiment, the GRV indicator may be introduced through the separate feeding tube. Note that this and other embodiments may be placed into the stomach before or after the feeding tube is placed in the stomach.

FIGS. 22-24 show another embodiment of the GRV measuring device which can be used in conjunction with a feeding tube after the feeding tube is already inserted. This embodiment is designed to go on the outside of a feeding tube and includes relatively stiff shaft 2208, sheath 2204, sensor(s) 2202 and slit 2206. Shaft 2208 may be made out of similar materials to shaft 2102 in FIG. 21. Sheath 2204 is preferably thin enough so that it can easily be slid over a feeding tube, yet rigid enough so that it does not collapse. Various polymers and other materials may be used. To introduce this embodiment after a feeding tube is already in place, sheath 2204 is placed over the outside of the proximal end of the feeding tube using slit 2206. The GRV measuring device is then slid down the outside of the feeding tube into the stomach of the patient using the relatively rigid shaft 2208.

FIG. 23 shows this embodiment of the GRV measuring device after it is placed over feeding tube 2302.

FIG. 24 is a cross sectional view of this embodiment of the GRV measuring device.

Figure 25:
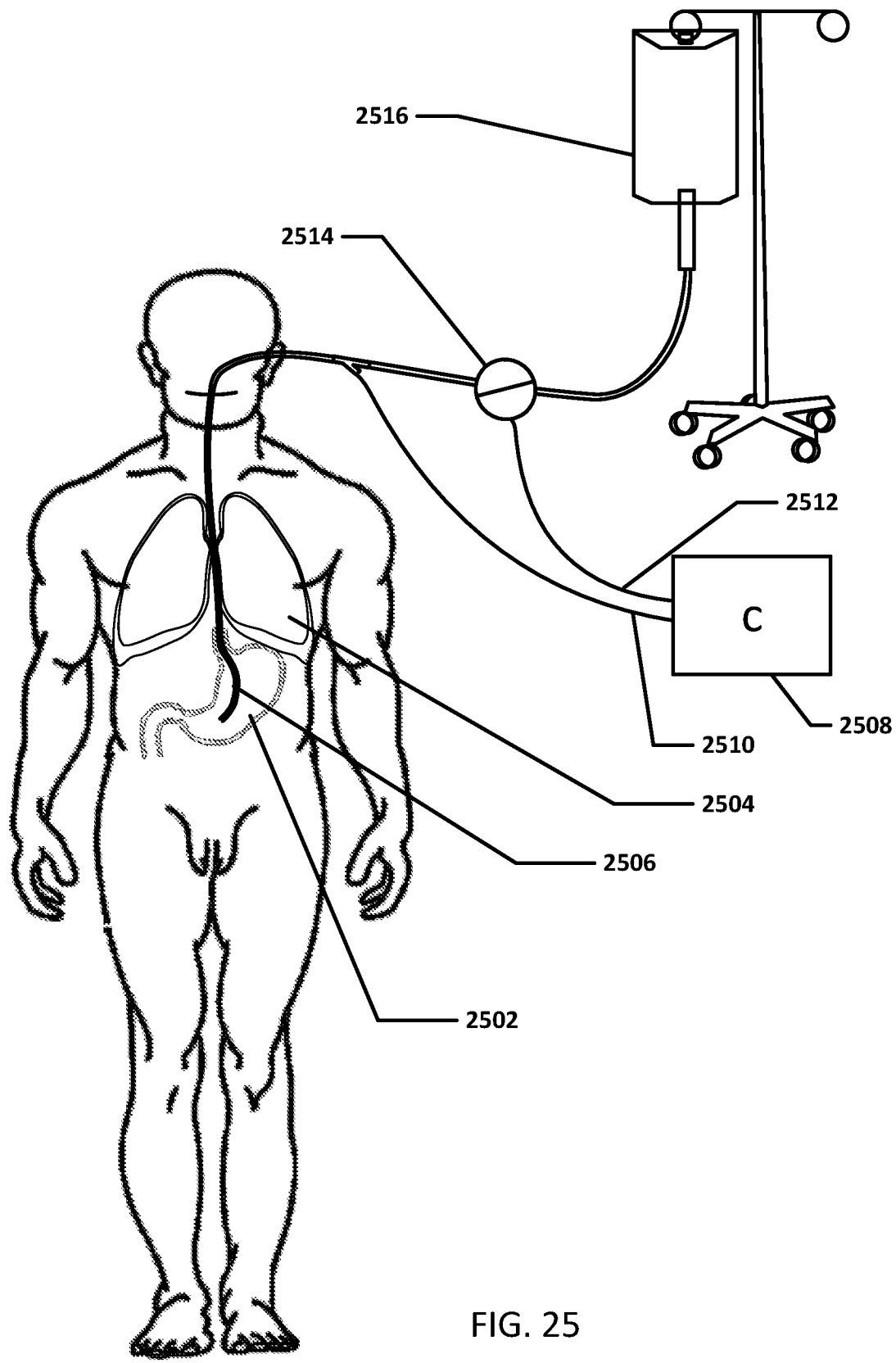
FIG. 25 shows an embodiment of the device where GRV and entry in the stomach is based on a continuously or intermittently monitored physical characteristic.

FIG. 25 shows an embodiment of the device where GRV and entry in the stomach is based on a continuously or intermittently monitored physical characteristic. In this embodiment, the GRV indicator may be inherent in the feed or meal itself. In this embodiment, the GRV indicator may be a physical characteristic such as temperature, pH, or electrical resistance, impedance or conductance, etc. In this embodiment, the physical characteristic may be monitored over time and the changes that occur as the meal empties from the stomach may be recorded. As the meal leaves the stomach and the relative concentration of gastric fluid increases the physical characteristic is altered in a measureable way. In one embodiment, the physical characteristic is pH wherein the pH decreases as the meal leaves the stomach and the gastric secretions represent more of what is left in the stomach. Once the pH reaches a sufficiently low level the device may alert the user that the meal has left the stomach and the patient is ready for another bolus. In another embodiment the physical characteristic is resistance or impedance. The meal delivered to the patient may be formulated to have high resistance or impedance so that subsequent decreases will indicate increasing concentration of gastric secretions. The opposite is true of conductance, which may increase as the meal leaves the stomach.

In yet another embodiment, the sensor may consist of a circuit that is powered by acid. For example, two leads may be introduced into the stomach consisting of different metals (in the preferred embodiment these are copper and magnesium) In the presence of acid, these metals act like the terminals of a battery and create a current. This current can be continuously or intermittently recorded and report the emptying of the stomach based on the increased concentration of acid. The same electrodes may also be used to sense the electrical parameters (impedance, conductance, resistance. Etc.) of the stomach to provide further information to help increase the sensitivity and specificity of the measurement. Each of these measurements of the physical characteristics of the stomach may be used, alone or in combination, to report that the sensor (and therefore the tube or catheter tip) is in the stomach and not in the lung. Ideally two or more parameters are measured (pH, current due to acid, impedance/conductance, etc.) to improve the accuracy of the measurement. This is important as the incidence of tube placement in the lung is as high as 20% and starting tube feeds with the tip in the lung can be fatal. In this embodiment, the sensors may be incorporated into the catheter/tube itself or may be a separate component that is threaded down the inside of an existing feeding catheter/tube to provide a spot reading as to the location of the tip of the tube. In the ideal embodiment, the sensor(s) is/are integrated into the catheter/tube to first provide an indication that the catheter/tube is in the stomach (and not the lung) and then provide a signal to indicate the GRV to help optimize feeding. In the ideal embodiment, as well, the feeding may be accomplished via a closed loop system that will automatically detect the GRV and deliver tube feed when appropriate based on the programmed nutritional goals for each patient. In this embodiment, target volumes of tube feed may be set per period of time and maximum volumes may be programmed.

FIG. 25 shows a patient with GRV measuring device 2506 placed in stomach 2502. Note the proximity of lungs 2504 and why it is important to be able to confirm placement of the GRV measuring device in the stomach, rather than the lungs or the esophagus. The GRV is measured as discussed herein. Controller 2508 may intermittently or continuously track the GRV via connector 2510 and using this information, control the feeding of the patient via valve or restrictor 2514 using connector 2512. Note that the connectors may be wired, as shown here, or wireless. Feed supply 2516 is connected to the feeding tube and the volume, rate, frequency, and content of the feed is controlled by controller 2508. GRV indicators may be inherent in the feed, added to the feed, or added independently of the feed. The controller may collect measurements of the GRV indicator inside the feeding tube, just before the feed is released into the stomach, as well as within the stomach contents over time. This provides the controller with a reading of the GRV indicator just before mixing begins, to provide an accurate GRV.

Note that the sensor(s) on the GRV measuring device may also be used to confirm placement of the GRV measuring device and/or feeding tube in the stomach, and not in the lungs or esophagus. For example, if the GRV indicator is pH or the presence of certain ions, these measurements will be different in the stomach, than they are in the lungs or esophagus, even before the GRV indicator is introduced into the feeding lumen. In this way, the GRV measuring device can determine placement of the feeding tube/device in the stomach and determine GRV. The sensors may be the same type of sensors, i.e. pH or ions, or there may be sensor(s) on the device for placement, and a separate type of sensor(s) for measuring the GRV indicator. For example, pH sensor(s) may measure placement of the device, and temperature sensor(s) may measure the GRV indicator (temperature) to determine GRV.

Figure 26:
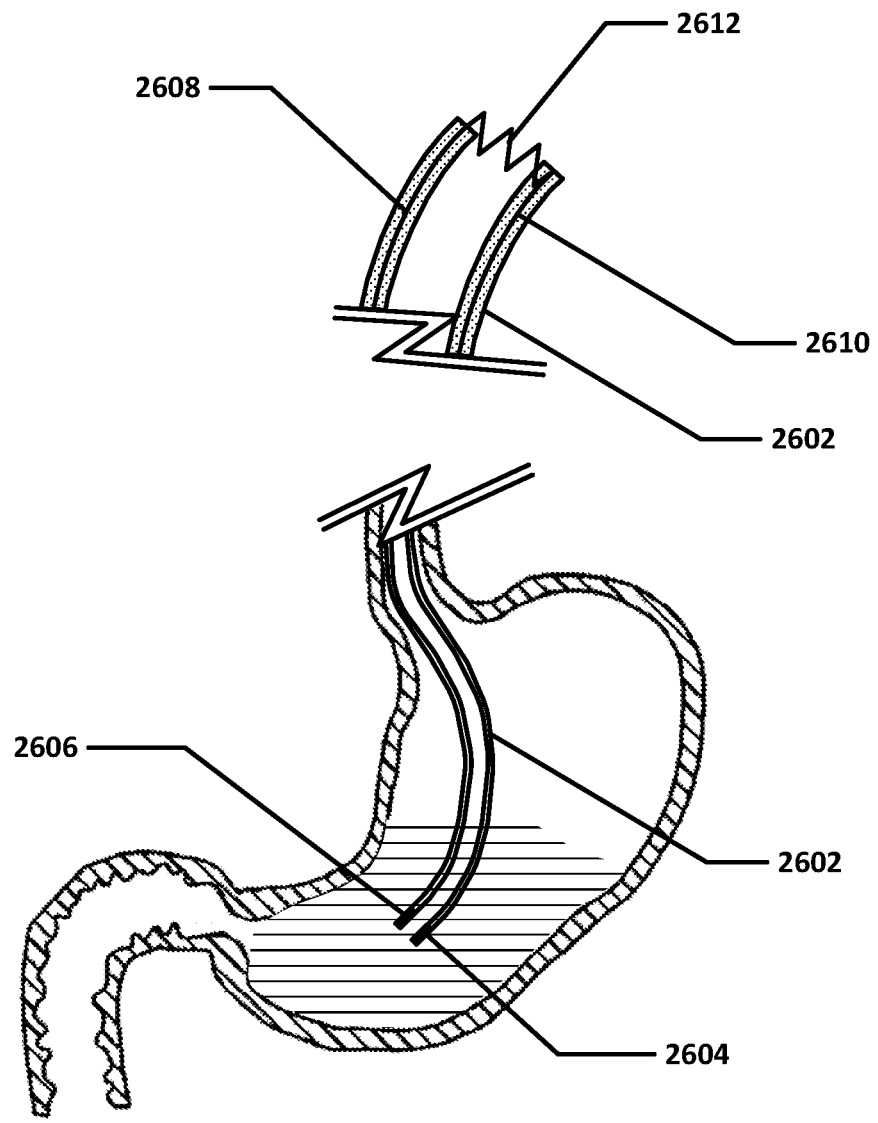
FIG. 26 shows an embodiment of the device

FIG. 26 shows an embodiment of the GRV measuring device which uses the gastric acid in the stomach to create a sort of battery which creates a measurable current which is measured and analyzed by a controller. The measured current is indicative of the GRV in the stomach. GRV measuring device shaft 2602 contains wires 2608 and 2610 which connect to two different electrodes, 2606 and 2604. The electrodes in this embodiment are made from dissimilar metals, such as Aluminum and Copper, but other dissimilar metals may be used. The current between the two electrodes is sensed by current sense resister 2612. In this embodiment, current is generated by the fluid in the stomach, and measured and analyzed by the controller to determine GRV.

In an alternative embodiment, the impedance of the stomach fluid is measured instead of current. The impedance is indicative of the ratio of gastric acid to feed, providing an estimate of GRV. This embodiment would look similar to the embodiment shown in FIG. 26 except that the electrodes would preferably be of the same metal rather than dissimilar metals. The controller would generate a voltage and measure the resulting current to determine the impedance of the fluid in the stomach. In this embodiment, voltage is generated by the controller, and current is passed through the fluid in the stomach and the resistance is measured and analyzed by the controller to determine GRV.

Using the different electrical properties of the gastric acid in the stomach and the feed, GRV can be estimated by conductivity, current, impedance, capacitance, electrical resistance etc. AC and/or DC signals can be used to make these measurements. Several possible embodiments are envisioned. For example:

In one embodiment, an additive liquid element (such as water, saline or similar) is introduced by the source that is significantly lower or significantly greater in temperature then the nominal content temperature. Measurement of the temperature may be recorded by sensors in one or more locations in the content mixture. In one embodiment, the rate of change in temperature over a period of time indicates the gastric volume. In one embodiment, the resulting temperature from the mixture after a set period of time indicates the gastric volume. In one embodiment, a physical thermal element introduces a sudden temperature change. This element quickly could heat or chill the gastric contents in contact with the element.

In one embodiment, an additive element is introduced that changes the viscosity of the contents. The resulting change in viscosity indicates the gastric volume. In one embodiment, the additive component glucose is introduced. The resulting change in concentration of glucose indicates the gastric volume. In one embodiment, coloring elements such as methylene blue is introduced and the resulting concentration is used to indicate gastric volume. In one embodiment, an additive component is introduced that changes the pH value of the gastric contents. The rate of change or resulting pH value indicates gastric volume. In one embodiment, an additive element is introduced that changes the conductivity of the contents. In one embodiment, an additive element is introduced that changes the refractive index, opacity, absorptivity, luminosity or color of the contents. In one embodiment, an additive element is introduced that changes the specific gravity of the contents.

In one embodiment, an additive component is introduced that causes the contents to change and is measure through a method of titration. In one embodiment, the additive component causes contents to solidify. In one embodiment, the additive component causes contents to change conductivity.

In one embodiment, the additive component causes contents to change optical opacity or color.

In one embodiment, pressure is introduced by introducing additional material into the gastric space. This material may be air, saline, water, or other. In one embodiment, pressure may be introduced by inflation of a balloon. In one embodiment, pressure response is measured internally. In one embodiment, pressure is measured externally with pressure gauges around the abdomen. This pressure difference before and after introduction will indicate volume.

In one embodiment, an acoustic source is used to produce standing waves in the gastric space. The resulting pattern of pressure indicates the dimensions of the media, in this case the gastric contents. In one embodiment, the acoustic source is external and an acoustic or pressure sensors are used internally. In one embodiment, both the source and sensors are internal. In one embodiment, the source is internal and the pressure or acoustic signature can be measured externally. In one embodiment, both the source and the sensor are external. The acoustic source may be a point source or an array of transducers that produce a range of frequencies and amplitudes. The acoustic or pressure sensor may be a single point of measurement or an array of sensors.

In one embodiment, the flow rate of material is measured directly in the pylorus transit. The stomach content volume is estimated through direct measurement of the input (enteral feeding material) and output (pylorus transit). In one embodiment, the amount of material entering and passing through the pylorus is measured with a volumetric flow meter. In one embodiment, Doppler ultrasound is used to measure fluid movement rate. In one embodiment, after magnetic materials are introduced into the stomach, the movement of the materials induces a current as it passes the pylorus transit. In one embodiment, optics are used to measure flow rate.

In one embodiment, an autonomous device travels within the gastric space to ensure all of the gastric contents are aspirated.

Example of Data Processing System

Figure 27:
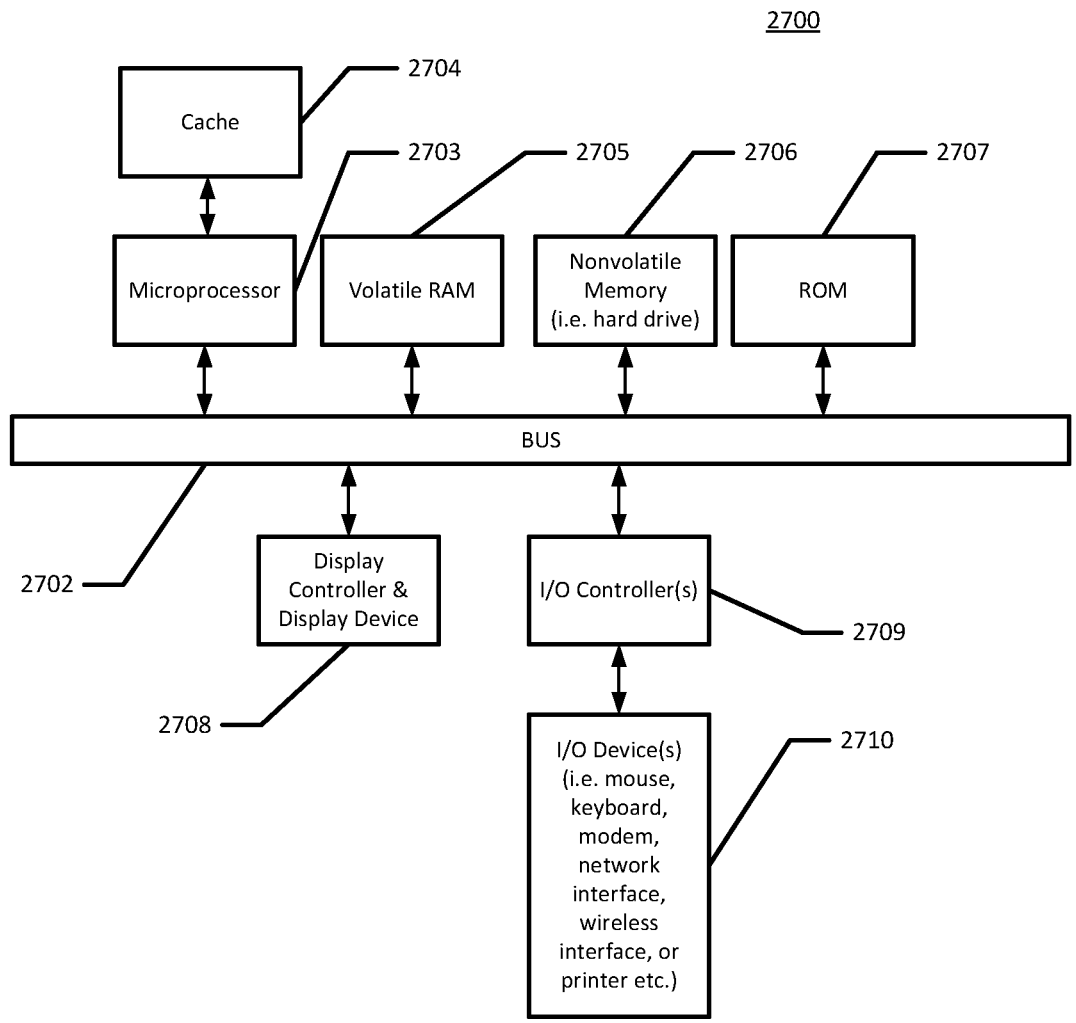
FIG. 27 is a block diagram of a data processing system, which may be used with any embodiments of the invention.

FIG. 27 is a block diagram of a data processing system, which may be used with any embodiment of the invention. For example, the system 2700 may be used as part of a controller which interprets the signals of the GRV measuring device. Note that while FIG. 27 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 27, the computer system 2700, which is a form of a data processing system, includes a bus or interconnect 2702 which is coupled to one or more microprocessors 2703 and a ROM 2707, a volatile RAM 2705, and a non-volatile memory 2706. The microprocessor 2703 is coupled to cache memory 2704. The bus 2702 interconnects these various components together and also interconnects these components 2703, 2707, 2705, and 2706 to a display controller and display device 2708, as well as to input/output (I/O) devices 2710, which may be mice, keyboards, modems, network interfaces, printers, and other devices which are well-known in the art.

Typically, the input/output devices 2710 are coupled to the system through input/output controllers 2709. The volatile RAM 2705 is typically implemented as dynamic RAM (DRAM) which requires power continuously in order to refresh or maintain the data in the memory. The non-volatile memory 2706 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 27 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 2702 may include one or more buses connected to each other through various bridges, controllers, and/or adapters, as is well-known in the art. In one embodiment, the I/O controller 2709 includes a USB (Universal Serial Bus) adapter for controlling USB peripherals. Alternatively, I/O controller 2709 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

What is claimed is:

1. An apparatus for determining a gastric residual volume (GRV), comprising:
    an elongate body having a length;
    one or more GRV sensors positioned along the elongate body, wherein the one or more GRV sensors are configured to measure a change in a GRV parameter when positioned within a body lumen of a subject;
    one or more placement sensors positioned along the elongate body, wherein the one or more placement sensors are configured to measure a change in a first physiological parameter and in a second physiological parameter when positioned within the body lumen, wherein the first and second physiological parameters comprise conductivity or impedance, and temperature; and
    a controller in communication with the one or more GRV sensors and the one or more placement sensors, wherein the controller is configured to determine a GRV based on the change in the GRV parameter, and wherein the controller is further configured to confirm a location of the elongate body within the subject during use based upon the change in the physiological parameter.

2. The apparatus of claim 1 further comprising a medium having one or more GRV indicators for introduction into the body lumen.

3. The apparatus of claim 1 wherein the controller is configured to determine the change in the GRV parameter or the first or second physiological parameter during positioning of the elongate body within the subject.

4. The apparatus of claim 1 wherein the controller is configured to determine the change in the GRV parameter or the first or second physiological parameter continuously.

5. The apparatus of claim 1 wherein the controller is configured to determine the change in the GRV parameter and the first or second physiological parameter continuously.

6. The apparatus of claim 1 wherein the one or more GRV sensors and the one or more placement sensors are the same.

7. The apparatus of claim 6 wherein the one or more GRV sensors and the one or more placement sensors are configured to sense impedance or conductivity.

8. The apparatus of claim 1 wherein at least one of the GRV sensors and the one or more placement sensors are different from one another.

9. The apparatus of claim 1 wherein the elongate body defines at least one lumen therethrough.

10. The apparatus of claim 9 wherein a medium having one or more GRV indicators is in fluid communication through the at least one lumen.

11. The apparatus of claim 9 wherein the one or more GRV sensors are positioned within the at least one lumen.

12. The apparatus of claim 11 wherein the controller is configured to measure an initial baseline GRV parameter from the one or more GRV sensors.

13. The apparatus of claim 1 wherein the one or more GRV sensors are positioned along an external surface of the elongate body.

14. The apparatus of claim 13 wherein the one or more GRV sensors are embedded along the external surface of the elongate body in a smooth transition.

15. The apparatus of claim 1 further comprising a restrictor in communication with the elongate body, wherein the restrictor is configured to control a flow of a medium through the elongate body.

16. The apparatus of claim 15 wherein the restrictor is configured to be controlled via the controller through a feedback loop.

17. The apparatus of claim 16 wherein the feedback loop comprises an upper cutoff limit.

18. The apparatus of claim 16 wherein the feedback loop comprises a lower cutoff limit.

19. The apparatus of claim 16 wherein the flow of medium is controlled based upon the GRV.

20. The apparatus of claim 15 wherein the controller is configured to meter the flow of the medium into boluses.

21. The apparatus of claim 15 wherein the controller is configured to meter the flow of the medium into a continuous flow.

22. The apparatus of claim 15 wherein the controller is configured to control a content of the medium.

23. The apparatus of claim 1 further comprising an inflatable balloon positioned along the elongate body and in communication with the controller.

24. A method of determining a gastric residual volume (GRV) in a body lumen, comprising:
measuring a change in a first physiological parameter and in a second physiological parameter within the body lumen via one or more placement sensors positioned along an elongate body, wherein the first and second physiological parameters comprise conductivity or impedance, and temperature;
confirming a location of the elongate body within the body lumen based upon the change in the first or second physiological parameter;
sensing a GRV parameter from a medium having one or more GRV indicators within the body lumen via one or more GRV sensors positioned along the elongate body;
monitoring the one or more GRV indicators for a change in the GRV parameter; and
determining a GRV of the body lumen based on the change in the GRV parameter.

25. The method of claim 24 further comprising introducing the medium having the one or more GRV indicators through the elongate body and into the body lumen prior to sensing the GRV parameter.

26. The method of claim 24 wherein monitoring the one or more GRV indicators comprises monitoring for the change in the GRV parameter or the first or second physiological parameter while positioning the elongate body within the body lumen.

27. The method of claim 24 wherein monitoring the one or more GRV indicators comprises monitoring for the change in the GRV parameter or the first or second physiological parameter continuously.

28. The method of claim 24 wherein monitoring the one or more GRV indicators comprises monitoring for the change in the GRV parameter and the first or second physiological parameter continuously.

29. The method of claim 24 wherein sensing the GRV parameter further comprises sensing the GRV parameter or the first or second physiological parameter.

30. The method of claim 29 wherein sensing the GRV parameter or the physiological parameter comprises sensing for impedance or conductivity.

31. The method of claim 24 wherein the one or more placement sensors and the GRV sensors are the same.

32. The method of claim 24 wherein sensing the GRV parameter comprises sensing via the one or more GRV sensors positioned within the elongate body.

33. The method of claim 32 further comprising measuring an initial baseline GRV parameter from the one or more GRV sensors.

34. The method of claim 24 wherein the one or more GRV sensors are positioned along an external surface of the elongate body.

35. The method of claim 34 wherein the one or more GRV sensors are embedded along the external surface of the elongate body in a smooth transition.

36. The method of claim 25 wherein introducing the medium comprises controlling a flow of the medium through the elongate body via a restrictor in communication with the elongate body.

37. The method of claim 36 wherein controlling the flow of the medium comprises controlling the restrictor through a feedback loop via a controller.

38. The method of claim 37 wherein the feedback loop comprises an upper cutoff limit.

39. The method of claim 37 wherein the feedback loop comprises a lower cutoff limit.

40. The method of claim 37 wherein the flow of medium is controlled based upon the GRV.

41. The method of claim 25 wherein introducing the medium comprises metering the flow of the medium into boluses.

42. The method of claim 25 wherein introducing the medium comprises metering the flow of the medium into a continuous flow.

43. The method of claim 25 wherein introducing the medium comprises controlling a content of the medium.

44. The method of claim 24 wherein the elongate body further comprises an inflatable balloon positioned along the elongate body.

* * * * *